United States Patent [19]

Barta et al.

[11] Patent Number: 4,814,174

[45] Date of Patent: Mar. 21, 1989

[54] TRANSDERMAL LAMINATED PHARAMACEUTICAL COMPOSITIONS HAVING PROLONGED EFFECT AND PROCESS FOR THE PREPARATION THEREOF

[75] Inventors: Irén Barta; Pál Fekete; László Pallos; Gábor Kovács; Lajos Mahr, all of Budapest, Hungary

[73] Assignees: Egis Gyogyszergyar; Muanyagipari Kutato Intezet, both of Budapest, Hungary

[21] Appl. No.: 101,623

[22] Filed: Sep. 28, 1987

[30] Foreign Application Priority Data

Sep. 26, 1986 [HU] Hungary .............................. 4117/86

[51] Int. Cl.$^4$ .............................................. A61F 13/02
[52] U.S. Cl. .................................. 424/448; 424/449; 427/171
[58] Field of Search ...................... 424/443, 448, 449

[56] References Cited

U.S. PATENT DOCUMENTS 4,486,193 12/1984 Shaw et al. ........................ 424/449
4,615,699 10/1986 Gale et al. ......................... 424/448
4,650,484 3/1987 Shaw et al. ........................ 424/448

Primary Examiner—Thurman K. Page
Assistant Examiner—L. R. Horne
Attorney, Agent, or Firm—Herbert Dubno; Jonathan Myers

[57] ABSTRACT

The invention relates to a transdermal laminated pharmaceutical composition (plaster) having prolonged effect, wherein one or more storing layer(s) comprising the active ingredient, an ethylene/vinyl acetate copolymer regulating layer and an adhesive layer are applied onto the carrier.

The pharmaceutical composition is prepared by coupling a carrier comprising the active ingredient with a regulating layer consisting of an ethylene/vinyl acetate copolymer foil having a vinal acetate content of 2-40 molar %. The foil is previously irradiated in a thickness of 100-300 μm with a high-energy irradiation in a dose of 1-15 Mrad—preferably with electron radiation—and thereafter stretched at 80°-90° C. to a thickness of 2-200 μm.

The system comprising the carrier and the regulating layer is subsequently coupled with an adhesive layer.

5 Claims, 2 Drawing Sheets

TRANSDERMAL LAMINATED PHARAMACEUTICAL COMPOSITIONS HAVING PROLONGED EFFECT AND PROCESS FOR THE PREPARATION THEREOF

This invention relates to transdermal laminated pharmaceutical compositions having prolonged effect and a process for the preparation thereof.

According to the present invention there are provided transdermal laminated pharmaceutical compositions (plasters) having prolonged effect wherein one or more storing layer(s) containing the active ingredient, a regulating layer based on an ethylene/vinyl acetate copolymer and an adhesive layer are applied onto a carrier.

Several processes are known for the preparation of transdermal pharmaceutical compositions having prolonged effect whereby synthetic polymers are used in order to provide a uniform and long-lasting delivery of the active ingredient. The said pharmaceutical compositions comprise a layer for the storing of the active ingredient from which the active ingredient diffuses toward the skin surface, and, if the said layer can not be fixed on the skin surface, also a separate adhesive layer. In addition to the above layers a further layer can be inserted between the storing layer and the skin, the said layer being permeable to the active ingredient and controlling the diffusion speed of the active ingredient. Transdermal plaster compositions prepared by the known methods generally contain a further layer which is made of a polymer and/or metal, is attached to the storing layer and serves for closing the side of the plaster opposite to the skin. Several patent specifications relate to such transdermal pharmaceutical compositions.

The polymer material of the layer storing the active ingredient varies from process to process, depending on the individual active ingredient.

Non-adhesive storing layers are disclosed in the U.S. Pat. Nos. 3,946,106; 3,992,518 and 4,053,580; the Japanese patent specifications Nos. 57 146,711 and 58 011 136 and the German patent specification No. 3,319,469. The pharmaceutical compositions prepared by the above methods are characterized by the common feature of long-lasting effect. The said compositions are, however, unsuitable for providing a uniform active ingredient delivery being constant in time.

Storing layers of adhesive character are set forth in the Japanese patent specifications Nos. 58-011,136; 57146,711 57 059 977; 57 075,917; 57 107,155; 57 123 117; 57 125,753 and 57 179,271. Although the pharmaceutical compositions prepared by the said methods have prolonged effect, no uniform active ingredient delivery is achieved. According to the Japanese patent specifications Nos. 59 084,811 and 59 084,813 and the published Dutch patent specification No. 82.01,034 a layer regulating the active ingredient delivery is applied which provides a uniform active ingredient delivery in addition to the prolonged effect. However, in these pharmaceutical compositions the character of the regulating polymer layer is to be selected on the basis of the quality of the active ingredient. The drawback of the above methods, wherein a regulating layer is used, resides in the fact that the amount of active ingredient delivered within a unit of time can be controlled only by modifying the surface of the plaster. This might cause dosage problems or the maintenance of a therapeutical level can require the use of an intolerably large surface.

It is the object of the present invention to provide a process which, under maintaining the advantages of polymers layers, particularly those of regulating polymer layers, used in the known methods, makes available transdermal pharmaceutical compositions wherein the active ingredient delivery required and sufficient to yield the desired therapeutical level can be achieved without modifying the surface of the composition.

The present invention is based on the recognition that if an ethylene/vinyl acetate copolymer foil subjected to high energy radiation (e.g. gamma or electron radiation) and subsequent stretching is used in a transdermal pharmaceutical composition as regulating layer, the amount of the active ingredient diffused through the said layer within a unit of time can be modified depending on the rate of irradiation and stretching.

The present invention is based on the further recognition that the ratio of the etylene and vinyl acetate monomer units forming the irradiated and streched copolymer foil also exerts an affect on the amount of the active ingredient diffused through the foil within a unit of time and the direction and strength of the said effect is influenced by the hydrophilic or hydrophobic character of the active ingredient.

It has also been found that, in case of a fixed ratio of monomers, the active ingredient delivery is significantly affected by the molecular weight of the polymer of the regulating layer, too.

It appears from the aforesaid that by careful harmonization of the above three factors the amount of the active ingredient diffused through the surface within a unit of time can be regulated in a manner which provides the desired therapeutical effect.

According to the process of the present invention such an ethylene/vinyl acetate copolymer foil subjected to high energy irradiations and subsequent stretching is used as regulating layer which comprises the ethylene and vinyl acetate monomers in a ratio and has a polymer molecular weight depending on the character of the acive ingredient and the therapeutical level to be achieved.

According to the process of the present invention as ethylene/vinyl acetate copolymer foil a laminated product is used which has a vinyl acetate content of 2–40 molar %, a thickness (before stretching) of 100–300 $\mu$m; and has a flow index (190/2.16) of 2–20 g/10 minutes.

According to the present invention there is provided a process for the preparation of a transdermal pharmaceutical composition (plaster) having prolonged effect wherein onto an impermeable metal and/or polymer carrier layer having a thickness of 50–200 $\mu$m one or more storing layer(s) containing 11–20% by weight of the active ingredient(s) is (are) applied, and onto the said storing layer(s) a regulating layer and finally a self-adhering layer having a thickness of 5–100 $\mu$m is applied.

Accordingn to the characteristic features of the process of the present invention as regulating layer an ethylene/vinyl acetate copolymer foil comprising 2–40 molar % of vinyl acetate is used, which has been previously subjected in a thickness of 100–300 $\mu$m to a high-energy radiation in a dose of 1–15 Mrad, preferably to electron radiation, and subsequently to an optional stretching to a thickness of 2–200 $\mu$m under thermal treatment at 90° C.

The foil thickness of the ethylene/vinyl acetate copolymer foil is preferably such that it should not be larger than the penetration depth of the high energy irradiation. Thus, after thermal treatment and stretching the regulating polymer layer exerts the diffusion inhibiting effect throughout the complete cross-section thereof.

One may, however, also proceed by using a copolymer foil of such a thickness that the penetration depth of the irradiation is only a part (one-half or even one-tenth) of the foil thickness. In this case the regulating (diffusion inhibiting) effect of the stretched foil is proportional to the thickness of the irradiated layer.

The active ingredient retaining effect of the regulating foil can also be influenced by the rate of stretching if the said rate of stretching amounts to 100/200 or 100/250 for larger active ingredient molecules and to 100/150 for smaller active ingredient molecules. In the case of an active ingredient of hydrophilic character (e.g. terbutaline sulfate) it is preferred to subject a copolymer foil having a higher vinyl acetate content (20–30 molar %) to irradiation, while for a hydrophobic active ingredient (e.g. nitroglycerol) it is expedient to irradiate a copolymer foil having a lower vinvyl acetate content (10–15 molar %).

The foil to be irradiated can also be prepared from an ethylene/vinyl acetate copolymer to which prior to foil formation (e.g. extrusion) in the case of a highly hydrophilic active ingredient a polyvinyl acetate homopolymer and for very hydrophobic active ingredients a polyethylene homopolymer was added. The presence of the homopolymers in the regulating foil can exert an effect on the permeability of the said foil.

According to a preferred form of realization of the process of the present invention one may proceed advantageously by introducing into the storing layer in addition to the active ingredient additives which facilitate the uniform diffusion of the active ingredient through the regulating layer (e.g. glycerol, vaseline oil) and/or enhance transdermal absorption (e.g. dimethyl sulfoxide, capsaicine).

The storing layer used in the process of the present invention can be at room or body temperature either solid, jelly-like (e.g. in the presence of polyvinyl alcohol or gelatine) or liquid adjusted to a suitable viscosity (e.g. in the case of a solution of the active ingredient in glycerol or in aqueous or oily emulsion and suspension). In the letter case the storing layer of the composition must be sealed at the plane of the layer by a welded joint or sticking.

The individual layers of the plaster prepared by the process of the present invention are attached to each other and, on use, to the skin without an air-gap. If the adhesion between the individual layers is insufficient, a separate adhesive layer is to be applied. If it, however, advisable to use an adhesive layer which is it permeable to the active ingredient. One may proceed preferably by using an acrylate-type water-based self-adhering adhesive for this purpose. The reverse-side of the composition (plaster) can be closed by a layer impermeable to the active ingredient and to the other low molecular substances being present in the composition. Thus, an aluminum foil preferably backed by one or more polymer(s) (e.g. polyvynylidene chloride, polyolefines, polyvinyl chloride, etc.) can be used.

According to the process of the present invention in the preparation of the transdermal pharmaceutical compositions no materials can be used which enter into chemical interaction with the active ingredient. Furthermore only such components (e.g. low molecular weight additives) can be used which enter into physical interaction (e.g. limited swelling) only with the material of the carrier layer and the regulating layer.

According to a preferred from of realization of the process of the present invention an aluminum foil backed by a polymer is jointed to 100 g of a storing layer containing 1–20 g of the active ingredient. This can be carried out by casting or sticking onto the aluminium foil. The irradiated and stretched regulating foil is attached to the other side surface of the storing layer. This can be accomplished with the aid of rolling for a storing matrix having a self-adhesive surface or by sticking in the case of an other type of a solid matrix or bag.

On using a liquid storing layer one or both sides of the welded bag can be prepared from the regulating copolymer foil according to the present invention. The self-adhesive sticking layer which fixes the plaster to the skin can be applied onto the surface of the regulating foil by laminar casting. The said fixing adhesive layer of the transdermal composition of the present invention can also be casted on the free surface of the closing foil, overreaching the storing layer, and in this case an adhesive, which can be concentricaly applied onto the plaster, directly presses the regulating foil to the skin.

The ethyl/vinyl acetate copolymer foil subjected to irradiation in the process of the present invention can be prepared from a powder-mixture or granules or blend (in the case of admixing homopolymer) by usual and conventional foil-forming methods of the plastic industry (e.g. by casting, precipitation, extrusion, foil-blowing). It is preferred to prepare the said copolymer foil of suitable composition by extrusion.

The advantages of the process of the present invention can be summarized as follows:

(a) The process is suitable for efficient formulation of active ingredients corresponding to a very wide range of polarity (i.e. hydrophilic/hydrophobic character) and molecular size.

(b) The process is technologically readily feasible by suitable combination of conventional equipment generally used in various branches of the industry.

(c) The pharmaceutical composition prepared by the process of the present invention provides a prolonged and uniform active ingredient delivery.

(d) The pharmaceutical composition of the present invention enables an exact adjustment of the dose providing the desired favorable therapeutical level.

(e) The pharmaceutical composition prepared according to the present invention provides a prolonged and uniform active ingredient delivery without undue increase of the active ingredient concentration in the storing layer. (The time-limit of uniform active ingredient delivery may coincide with the point of time of exhaustion of the storing layer.)

(f) The process of the present invention eliminates the necessity of increasing the surface of the composition because a suitable dose of active ingredient delivery can be obtained without enlarging the said surface, too.

(g) The pharmaceutical composition of the present invention enables the modification of the dosage of the active ingredient without changing the composition of the regulating foil.

(h) According to the process of the present invention it is possible to apply from the same surface different amounts of active ingredient onto the skin, whereby the time-consuming and expensive re-adjustment of the manfucturing equipment is eliminated.

(i) The process of the present invention enables the use of regulating foils of identical type for the preparation of transdermal compositions containing different active ingredients.

According to a further aspect of the present invention there are provided pharmaceutical compositions (transdermal plasters) prepared according to the above process of the present invention.

DETAILED DESCRIPTION OF THE DRAWING

Figure 1:
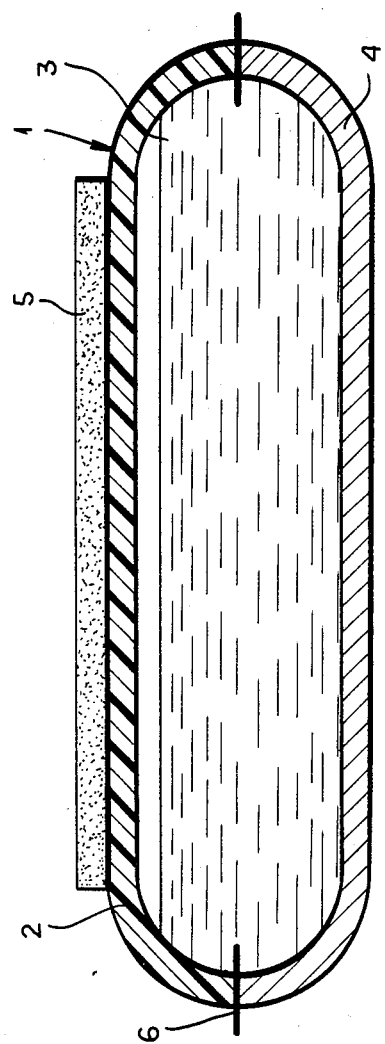
FIG. 1 is a sectional view through the transdermal laminate according to one preferred feature of the invention.

According to FIG. 1, the transdermal laminate pharmaceutical composition 1 of the present invention comprises a carrier layer 4 impervious to a pharmaceutically active ingredient contained in said composition, a regulating layer 4 bonded at its ends to the ends of the carrier layer 4 thereby forming a sealed bag 6 which surrounds a liquid storing layer 3 containing a matrix impregnated with the pharmaceutically active ingredient. The regulating layer has been previously subjected to high energy radiation and then to optional stretching in order to determine its permeability for the pharmaceutically active ingredient.

Though the carrier layer is impervious to the pharmaceutically active ingredient contained in the storing layer, the regulating layer has the ability to let the pharmaceutically active ingredient contained in the storing layer pass through at a predetermined, controlled rate.

An adhesive layer 5 is bonded to the opposite surface of the regulating layer from the surface bonded to the carrier layer. The adhesive layer permits adherence of the laminate pharmaceutical composition to the skin of a patient in need of the pharmaceutically active ingredient. The adhesive layer of course must be permeable to the pharmaceutically active ingredient.

Figure 2:
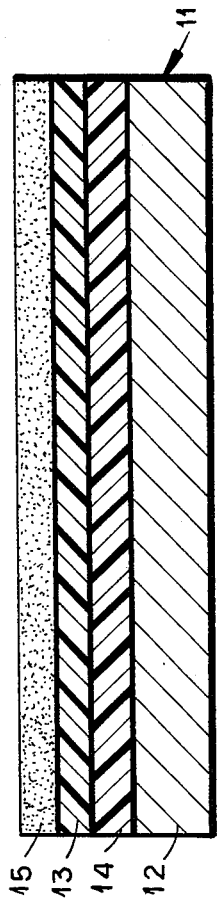
FIG. 2 is a sectional view through the transdermal laminate according to a second preferred feature of the invention.

In FIG. 2 the transdermal laminate pharmaceutical composition 11 of the present invention comprises a carrier layer 12 impervious to a pharmaceutically active ingredient contained in said composition and a storing layer 14 bonded to said carrier layer. The storing layer as applied to the carrier layer may be either a solid or liquid and contains the pharmaceutically active ingredient. Next a regulating layer 13 is applied to the surface of the storing layer opposite the storing layer surface bonded to the carrier layer 12. The regulating layer has the ability to let the pharmaceutically active ingredient contained in the storing layer pass through a predetermined, controlled rate because as in the case as described for FIG. 1, the regulating layer has been previously treated with high energy radiation and optional stretching.

An adhesive layer 15 is bonded to the opposite surface of the regulating layer from the surface bonded to the storing layer. The adhesive layer permits adherence of the laminate pharmaceutical composition to the skin of the patient in need of the pharmaceutically active ingredient. The adhesive layer of course must be permeable to the pharmaceutically active ingredient.

Further details of the present invention are to be found in the following Examples without limiting the scope of protection to the said Examples.

EXAMPLE 1

Onto the PE (polyethylene) side of a triple-laminated (Triplex) foil (consisting of a 60 $\mu$m polyethylene (PE), 15 $\mu$m Al and 20 $\mu$m bi-oriented polypropylene (BOPP) layer) 0.8 g of a matrix containing nitroglycerol is laminated. The said matrix is obtained by admixing 13.75 g of lactose comprising 10% by weight of nitroglycerol, 16.5 g of lactose and 13.75 g of a 10% by weight aqueous solution of polyethylene glycol 400 in a mortar. A regulating foil is placed on the matrix. The said regulating foil is extruded from an ethylene/vinyl acetate granular copolymer [the molar % of vinyl acetate amounts to 8-10; flow index (190/2.16)=2-3 g/10 minutes] to a thickness of 120 $\mu$ and irradiated in a betatron at a current density of 6.05 $\mu$A/cm$^2$ for 6 seconds in four stokes. The transferred dose amounts to 12 Mrad which results in a 40% cross-linking of the foil (measured according to ASTM D 2675). The foil is then subjected to a 100/150 rate longitudinal stretching under heating on a water-bath at 90° C. After stretching the thickness of the foil amounts to 70$\mu$. The regulating foil is welded with the polyethylene side of the Triplex foil in a foil-welder at 180° C. so that the matrix remains in the "bag" formed and the size of the surface of the "bag" coated with the ethylene/vinyl acetate (EVA) copolymer amounts to 10 cm$^2$. The ethylene/vinyl acetate surface of the "bag" is coated with an aqueous acrylate-based self-adhering adhesive having a dry substance content of 56.5-57% by weight, a pH value of 7.5-8 and a density of 0.886 g/cm$^3$.

From the plaster thus obtained the active ingredient delivery is $2.6 \cdot 10^{-5}$ g/cm$^2$/h and remains constant for 48 hours (measured according to Prakash R. Keshamy and Yie W. Chien: Drug Development and Industrial Pharmacy 10/6, 883-913 (1984)). This enables the delivery of 6 mg of nitroglycerol from a surface of 10 cm$^2$ within 24 hours.

EXAMPLE 2

The laminated coupled system according to Example 1 is prepared except that the regulating foil is extruded from an ethylene/vinyl acetate granular copolymer having a different composition [molar % of vinyl acetate=27-30; flow index (190/2.16)=17-25 g/10 min] to a thickness of 150$\mu$. The foil is irradiated under the conditions disclosed in Example 1 with an energy of 15 Mrad five times (in five strokes). The rate of cross-linking amounts to 70%. The irradiated foil is stretched at a rate of 100/200 at 90° C. According to in vitro measurement from the plaster thus obtained nitroglycerol is delivered at a constant rate of $4.2 \cdot 10^{-5}$ g/cm$^2$/h for 36 hours. This enables a nitroglycerol delivery of 10 mg from a surface of 10 cm$^2$ within 24 hours.

EXAMPLE 3

The coupled system according to Example 1 is built up by using a regulating layer having the composition disclosed in Example 1 [molar % of vinyl acetate=8-10; flow index (190/2.16)=2-3 g/10 minutes] to a thickness of 200$\mu$. The foil is irradiated under the contditions described in Example 1 with an energy of 15 Mrad five times (in five strokes).

Rate of cross-linking=70%. The foil is used without stretching. According to in vitro measurement a constant nitroglycerol delivery of $1.04 \cdot 10^{-5}$ g/cm²/h is obtained for 48 hours. This enables a nitroglycerol delivery of 2.5 mg from a surface of 10 cm² within 24 hours.

EXAMPLE 4

A coupled system according to Example 1 is prepared except that the regulating layer is extruded from an ethylene/vinyl acetate granular copolymer having a different composition [molar % of vinyl acetate=18-20; flow index (190/2.16)=2-3 g/10 minutes] to a thickness of 150 μ. The foil is irradiated under the conditions disclosed in Example 1 with an energy of 15 Mrad successively five times (in five strokes). Rate of cross-linking=70%. The foil is stretched longitudinally at a rate of 100/200 at 90° C. The foil thus obtained having a thickness of 70 μ is used as regulating membrane. According to in vitro measurements from the composition thus obtained a constant nitroglycerol delivery of $9.84 \cdot 10^{-5}$ g/cm/h takes place for 18 hours. (The linearity of the nitroglycerol delivery can be improved by increasing the nitroglycerol content of the storing layer.) This enables a nitroglycerol delivery of 23 mg from a surface of 10 cm² within 24 hours.

EXAMPLE 5

45 g of a dispersion is casted on the aluminum side of a double-laminated edged 18×14 cm foil consisting of a 20μ thick Al and a 20μ thick bi-oriented polypropylene (BOPP) foil. The said dispersion is prepared by admixing 45 g of an aqueous polymer emulsion (dry substance content 50% by weight; vinyl acetate content 60% by weight; dubutyl maleate content 40% by weight) with 3 g of glycerol and 14 g of lactose comprising 10% by weight of nitroglycerol. The dispersion thus obtained is dried on a levelled plate to an air-dry state. After drying an acrylate-based aqueous self-adhering adhesive layer is applied, which serves to fix a regulating foil described in Example 1 to the layers. The regulating foil is coated with a self-adhering adhesive in order to fix to the skin (see Example 1). The plate (18×14 cm) thus obtained is cut to 10 cm² pieces. According to in vitro measurement a constant nitroglycerol delivery of $2.5 \cdot 10^{-5}$ g/cm/h takes place for 60 hours. The results are consistent with those obtained according to Example 1, which is not surprising because an identical regulating foil is used. The longer linearity is due to the higher nitroglycerol content of the storing layer (50 mg/10 cm²).

EXAMPLE 6

The layers are built up according to Example 5 until the sticking of the regulating foil, except that 0.7 g of 2-tert. butylamino-1-(3,5-dihydroxypheryl)ethanol is used as starting material.

The regulating foil is prepared as follows:

10% by weight of a granular copolymer ethylene/vinyl acetate copolymer [molar % of vinyl acetate=1-8-20; flow index (190/2.16)=2-3 g/10 minutes] are admixed with a vinyl acetate homopolymer under mechanical stirring. From the mixture thus obtained a foil having a thickness of 150 μ is prepared by extrusion and the foil is irradiated under the conditions disclosed in Example 1 with a dose of 15 Mrad five times (in five strokes). Rate of cross-linking=40%. The irradiated foil is longitudinally stretched at 90° C. at a rate of 100/200. The regulating foil (thickness 70μ) thus obtained is fixed and provided with a self-adhering adhesive as described in Example 5. The active ingredient delivery of the plaster thus obtained amounts to $8 \cdot 10^{-6}$ g/cm²/h for 48 hours. This enables an active ingredient deliveyr of 2 mg within 24 hours.

EXAMPLE 7

The plasters according to Examples 1-6 are fixed to the skin by fixing the said compositions from the side of the closing layer to a self-adhesive tape so that the said self-adhesive tape should overreach the plaster at least by 1 cm on each side. The free part of the self-adhesive layer fixes the plaster to the skin and the moisture content of the skin forms a direct contact between the skin and the plaster. The above change of the art of fixing does not exert any effect on the other characteristics of the composition.

The characteristics of the pharmaceutical compositions prepared according to the previous Examples are composed to those of known compositions used for similar purposes and the results are summarized in Table 1.

TABLE 1

| Composition (manufacturer) | Surface (cm²) | Amount of delivered nitroglycerol (mg/24 hours) |
|---|---|---|
| Transderm-Nitro-5 (CIBA) | 10 | 5 |
| Transderm-Nitro-10 (CIBA) | 20 | 10 |
| Nitro-Our-5 (Key) | 5 | 2.5 |
| Nitro-Our-10 (Key) | 10 | 5.0 |
| Nitro-Our-15 (Key) | 15 | 7.5 |
| Nitro-Our-20 (Key) | 20 | 10 |
| Nitrodisc-16 (Searle) | 8 | 5 |
| Nitrodisc-32 (Searle) | 16 | 10 |
| Example 3. | 10 | 2.5 |
| Example 1. | 10 | 5 |
| Example 2. | 10 | 10 |
| Example 4. | 10 | 23 |

The above data regarding the known products are disclosed in the article of N.H. Parikh, A. Babar, F. M. Plakogiannis: Pharm. Acta. Helv. 60, No. 2 (1985).

As it clearly appears from the data of Table 1, in the case of the hitherto known compositions the amount of the delivered active ingredient was always regulated by modifying the surface of the composition. The dose of the active ingredient could be doubled by increasing the useful surface of the composition to the double. On the other hand, by using the coupled system of the present invention the size of the composition must not be changed any more; from a 10 cm² surface 2.5-23 mg of nitroglycerol can be delivered and this corresponds to the therapeutical level required.

EXAMPLE 8

The coupled system according to Example 1 is prepared except that the matrix is obtained by admixing 20 g of lactose containing 10% by weight of nitroglycerol with 20 g of propylene glycol (Fluka AG PRACT) in a mortar. According to in vitro measurement a constant nitroglycerol delivery of $2.6 \cdot 10^{-5}$ /g/cm²/h is obtained for 24 hours.

What we claim is:

1. A plaster for transdermal delivery of a pharmaceutical composition having a sustained effect, comprising at least one storing layer containing pharmaceutically active ingredient active ingredient, regulating layer and adhesive layer applied onto a carrier, wherein said regulating layer is an ethylene/vinyl acetate copolymer foil having a vinyl acetate content of 2 to 40 molar %, the said foil being previously irradiated in a thickness of 100 to 300 μm with a high-energy radiation in a dose of 1 to 15 Mrad and thereafter stretched at 80° to 90° C. to a thickness of 2 to 200 μm.

2. A process for the preparation of a plaster for transdermal delivery of a pharmaceutically active ingredient having a sustained effect from at least one storing layer containing the active ingredient, regulating layer and adhesive layer applied onto a carrier, which comprises using as regulating layer an ethylene/vinyl acetate copolymer foil having a vinyl acetate content of 2 to 40 molar %, the said foil being previously irradiated in a thickness of 100 to 300 μm with a high-energy radiation in a dose of 1 to 15 Mrad and thereafter stretched at 80° to 90° C. to a thickness of 2 to 200 μm.

3. Process according to claim 2, which comprises using an electron irradiated foil.

4. Process according to claim 2, which comprises stretching the ethylene/vinyl acetate copolymer foil after irradiation to a thickness of 70–120 m.

5. Transdermal pharmaceutical laminate having prolonged effect whenever prepared by the process according to claim 2.

* * * * *